United States Patent [19]

Elghazzawi

[11] Patent Number: 5,365,933
[45] Date of Patent: Nov. 22, 1994

[54] APPARATUS AND METHOD FOR DISTINGUISHING HEART BEATS FROM INTRA-AORTIC BALLOON PUMP BEATS

[75] Inventor: Ziad Elghazzawi, Roslindale, Mass.

[73] Assignee: Siemens Medical Systems, Inc., Danvers, Mass.

[21] Appl. No.: 30,927

[22] Filed: Mar. 12, 1993

[51] Int. Cl.⁵ .............................................. A61B 5/04
[52] U.S. Cl. ...................................... 128/697; 600/18
[58] Field of Search .................. 128/697, 672, 673; 600/16–18; 623/3

[56] References Cited

U.S. PATENT DOCUMENTS

| | | | |
|---|---|---|---|
| 4,174,707 | 11/1979 | Link et al. | 128/681 |
| 4,777,959 | 10/1988 | Wallach et al. | 128/677 |
| 4,867,171 | 9/1989 | Yamaguchi | 128/680 |
| 4,877,035 | 10/1989 | Bogen et al. | 128/673 |
| 5,030,197 | 7/1991 | Kageyama | 600/16 |
| 5,139,028 | 8/1992 | Steinhaus et al. | 128/697 |
| 5,158,529 | 10/1992 | Kanai | 600/18 |

OTHER PUBLICATIONS

"Design and Validation of an Algorithm to Extrat Arterial Blood Pressure Features During Intra-Aortic Balloon Pump Assist", Elghazawwi et al., 1991, Journal of Clinical Monitoring, vol. 7, pp. 97–98.

Primary Examiner—Lee S. Cohen
Assistant Examiner—Jeffrey R. Jastrzab
Attorney, Agent, or Firm—Lawrence C. Edelman

[57] ABSTRACT

A method and apparatus for distinguishing heart beats from intra-aortic balloon pump beats, and for distinguishing assisted heart beats from unassisted heart beats. The method and apparatus further allows for determining average minimum and maximum pressures of assisted and unassisted heart beats and the average maximum pressures of the balloon pump beats. In general, an embodiment of the invention distinguishes among assisted heart beats, unassisted heart beats, and balloon pump beats by a comparison of areas associated with portions of the arterial pressure waveform representative of each successive beat.

17 Claims, 3 Drawing Sheets

APPARATUS AND METHOD FOR DISTINGUISHING HEART BEATS FROM INTRA-AORTIC BALLOON PUMP BEATS

BACKGROUND OF THE INVENTION

The present invention relates to an apparatus and method for the identification of assisted and unassisted heart beats during intra-aortic balloon pump assistance, and in addition, to a means for determining the true arterial systolic and diastolic pressures during intra-aortic balloon pump assistance.

The intra-aortic balloon pump ("IABP") is used as a means of temporary mechanical support of the left ventricle to treat several forms of heart disease. During IABP support, clinicians are guided for assessment of patient conditions by monitoring various cardiac parameters including arterial pressure, cardiac index, pulmonary artery wedge pressure and pulmonary capillary wedge pressure. The monitoring of these cardiac parameters is also important for the weaning of the heart from IABP support. The measurement of arterial pressure is affected by IABP support and can thus provide misleading information as to the true condition of an individual's heart.

Arterial blood pressure measurement, for example, is used to determine the diastolic pressure (low pressure) and the systolic pressure (high pressure) of the heart. Existing methods of monitoring arterial pressure identify the diastolic and systolic pressures as the minima and maxima of the arterial pressure waveform. However, during IABP support the inflation and deflation of the intra-aortic balloon in the descending thoracic aorta during diastole creates an extra beat on the arterial blood pressure waveform next to the heart beat in the same cardiac cycle. The existing cardiovascular monitoring systems do not distinguish between the heart beat and the balloon beat during IABP support, and as a result, these monitoring systems average the high pressure of the balloon with the systolic pressure of a patient's heart, and average the dicrotic notch with the diastolic pressure of a patient's heart. This averaging results in the determination of erroneous values for arterial systolic and diastolic pressures, and thus the condition of a patient's heart is not accurately monitored.

Several types of artifact rejection methods have been described for use in determining true blood pressure values. One such approach uses sphygmometric blood pressure monitoring (see, for example, U.S. Pat. Nos. 4,174,707 and 4,777,959) and another approach uses the recognition and discrimination amongst Korotokoff sounds in the measurement of blood pressure to reject artifacts and to determine minimum and maximum pressures (see, for example, U.S. Pat. No. 4,867,171). One blood pressure detection method has been developed for use during intra-aortic balloon pump assist to separate heart beats from balloon beats: however this method requires the R—R interval values and QRS timing from an ECG beat detector in order to determine whether an arterial blood pressure beat is a balloon beat or a heart beat (Elghazzawi et al., 1991, *Jour. of Clinical Monitoring*, Vol. 7, pp. 97–98).

It is the purpose of the present invention to overcome the aforementioned difficulties in monitoring the condition of a patient's heart, and to provide a physician with accurate information to be used in assessing the progress of a patient's recovery.

SUMMARY OF THE INVENTION

The invention is an apparatus and a method for use in identifying heart beats and intra-aortic balloon pump beats during the procedure of intra-aortic balloon pump assist. Further, the invention is an apparatus and method for identifying assisted heart beats, unassisted heart beats, and intra-aortic balloon pump beats during the procedure of intra-aortic balloon pump assist, and for determining the average minimum and maximum pressures of assisted and unassisted heart beats and the average maximum pressures of the balloon pump beats.

In general, an apparatus embodying the method of the invention includes a pressure transducer that is responsive to arterial blood pressure beats to generate a time varying pressure signal, electronic circuitry connected to the pressure transducer to receive and process the pressure signal, and a display that is connected to the circuitry to display the processed pressure signal or a calculated pressure value associated therewith. The circuitry is adapted to determine successive minimum pressure values and maximum pressure values of the pressure signal; to determine a first and second portion of a beat, in which the first portion of a beat begins at a minimum pressure value and ends at an immediately succeeding maximum pressure value and the second portion of a beat begins at the maximum pressure value and ends at the next minimum pressure value; calculate respective first and second values for an attribute of the pressure signal over a time during the first and second portions of a first beat; calculate respective first and second values for an attribute of the pressure signal over a time during the first and second portions of a second beat which consecutively follows said first beat; compare the first value calculated for the first beat with the second value calculated for the first beat; compare the first value calculated for the second beat with the second value calculated for the second beat; and, based upon the comparison, to identify the second beat as one of a group comprising an intra-aortic balloon pump beat, a heart beat or an artifact. In a preferred embodiment, the second beat is identified as an intra-aortic balloon pump beat when the first value calculated for the first beat is greater than the second value calculated for the first beat, and the first value calculated for the second beat is less than the second value calculated for the second beat. A display is connected to the circuitry to display at least one pressure value of an identified beat.

In the preferred embodiment the attribute is the amplitude of the pressure signal, and the calculated first and second values correspond to areas associated with a pressure waveform representative of said pressure signal.

In further preferred embodiments the apparatus identifies a heart beat as an unassisted heart beat or an assisted heart beat. The circuitry is adapted to identify a heart beat as an assisted heart beat when the heart beat immediately follows an intra-aortic balloon pump beat. The display displays at least one of a minimum pressure value and a maximum pressure value of an unassisted heart beat, a minimum pressure value and a maximum pressure value of an assisted heart beat, and a maximum pressure value of an intra-aortic balloon pump beat.

In further preferred embodiments the circuitry is adapted to determine an average minimum pressure value and an average maximum pressure value for a plurality of unassisted heart beats, and to determine an average minimum pressure value and an average maximum pressure value for a plurality of assisted heart beats, and to determine an average maximum pressure value for a plurality of intra-aortic balloon pump beats. In some preferred embodiments an average minimum pressure value is determined by averaging at least eight minimum pressure values of an identified beat type after excluding the highest one-quarter and lowest one-quarter of the minimum pressure values, and an average maximum pressure value is determined by averaging at least eight maximum pressure values of an identified beat type after excluding the highest one-quarter and the lowest one-quarter of the maximum pressure values.

In further preferred embodiments the circuitry is adapted to determine the average heart beat rate and the display displays the average heart beat rate.

In further preferred embodiments, the method includes the step of determining the average heart beat rate based upon the frequency of identified heart beats.

A physician can use the average pressure values of the assisted and unassisted heart beats to monitor the recovery progress of a patient's heart. The average balloon beat maximum pressure value, or peak pressure measurement, can be used to monitor the effect of a balloon beat on a patient's arterial pressure, and can be used to determine appropriate balloon beat maximum pressure values.

In further preferred embodiments, the arterial blood pressure signal can be measured by invasive means. Arterial pressure can be measured by invasive means by placing a pressure sensor in one of several arteries, including the radial artery, the aorta, or the brachial artery. Alternatively, non-invasive methods can be used, such as a pulse oximeter, for developing a pressure signal.

In further preferred embodiments the minima and the maxima of the signal are determined using the first derivative of the signal.

In further preferred embodiments, the first value calculated for the first portion of a beat can be determined by multiplying the difference between the minimum and maximum value of the first portion of the beat by the length of time between the occurrence of the minimum value and the maximum value. In preferred embodiments the second value calculated for the second portion of a beat can be determined by multiplying the difference between the maximum value and the next minimum value of the second portion of the beat with the length of time between the occurrence of the maximum and next minimum value.

In further preferred embodiments, the first value calculated for the first portion of a beat can be determined by summing the values of the measured arterial pressure signal from the minimum value to the maximum value; and the second value calculated for the second portion of beat can be determined by summing the values of the measured arterial pressure signal from the maximum value to the next minimum value.

PREFERRED EMBODIMENTS

DETAILED DESCRIPTION OF THE INVENTION

Figure 1:
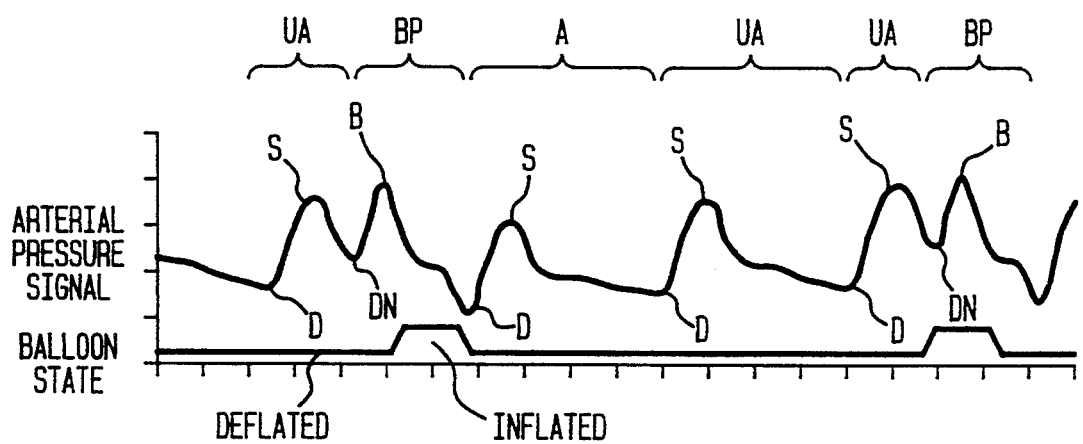
FIG. 1 is a diagram of an arterial blood pressure waveform representative of the measured arterial blood pressure during intra-aortic balloon pump assist.

Referring now to FIG. 1, a diagram of an arterial blood pressure waveform during intra-aortic balloon pump assist, and the state of the intra-aortic balloon is shown. The minimum, or diastolic point, of the arterial pressure is indicated by the symbol "D", the maximum, or systolic point, of the arterial pressure is indicated by the symbol "S", the dicrotic notch is indicated by the symbol "DN" and the intra-aortic balloon pump peak or maximum pressure is indicated by the symbol "B". The "first portion" of a beat, as that terms is used herein, is from a valid minimum point to an immediately succeeding valid maximum point, and the "second portion" of a beat, as that term is used herein, is from this maximum point to the immediately succeeding valid minimum point. As can be seen in FIG. 1, a minimum point can be a diastolic point or a dicrotic notch, and a maximum point can be a heart beat systolic point or a balloon beat peak pressure. The different types of beats are identified in FIG. 1, above the arterial pressure waveform. The designations are not overlapping, for the purposes of clarity, but it would be obvious to one of ordinary skill in the art that a succeeding beat begins immediately at the end of the diastolic period of a preceding beat. The symbol "UA" is used to designate an unassisted beat, which is a true heart beat and provides an estimate of the activity of the heart. The symbol "BP" is used to designate an intra-aortic balloon pump beat, which is the pressure produced by the intra-aortic balloon pump. The symbol "A" is used to designate an assisted heart beat, which is a beat that follows immediately after an intra-aortic balloon pump beat, and typically has a depressed systolic and diastolic pressure when compared to an unassisted heart beat.

Figure 3:
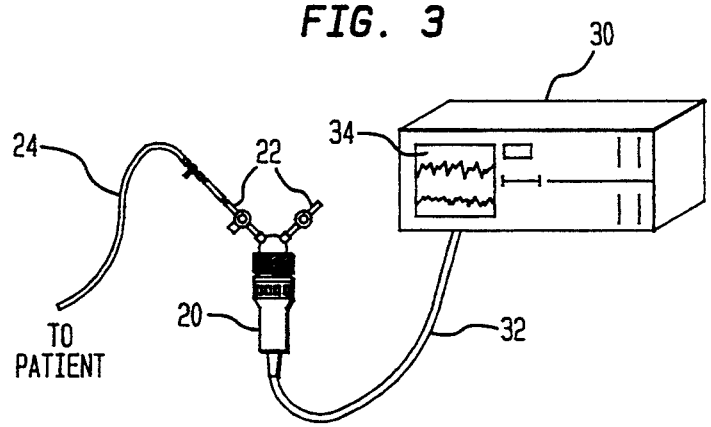
FIG. 3 shows a pressure transducer and a digital processor.

In a patient that is being treated with intra-aortic balloon pump assist, the condition of the patient's heart can be monitored by use of a pressure transducer that receives the arterial pressure wave signal of the patient's arterial blood pressure, and a processor that is programmed to process and display the arterial pressure signal that is transmitted to the processor from the pressure transducer. With reference now to FIG. 3, a pressure transducer 20 for connection to a patient, not shown, and to a processor 30 having a display 34 is shown. A pressure transducer, such as the one shown, has stopcocks 22, one of which can be connected to a patient by means of tubing 24 and the other of which can be referenced to air. The transducer sends the detected arterial pressure signal to the processor 30 by means of a cable 32. A pressure transducer is typically placed at the midchest level of a patient in order to negate the effects of hydrostatic pressure. Alternatively, a pressure transducer can be suspended at other levels, and the hydrostatic pressure negated by the use of a pressure bag, as is well known in the art. Quartz pressure transducers may also be employed, and such transducers can be attached directly to a patient's arm. Suitable transducers for use in the apparatus and method of the invention include Spectramed model nos. P23XL/4, P10EZ/4 and DT-XX available from Viggo-Spectramed, Inc., 1900 William Drive, Oxnard, Calif. 93030. In use with this method, the arterial blood pressure waveform is generally sampled 100 to 200 times per second for further processing.

Figure 4:
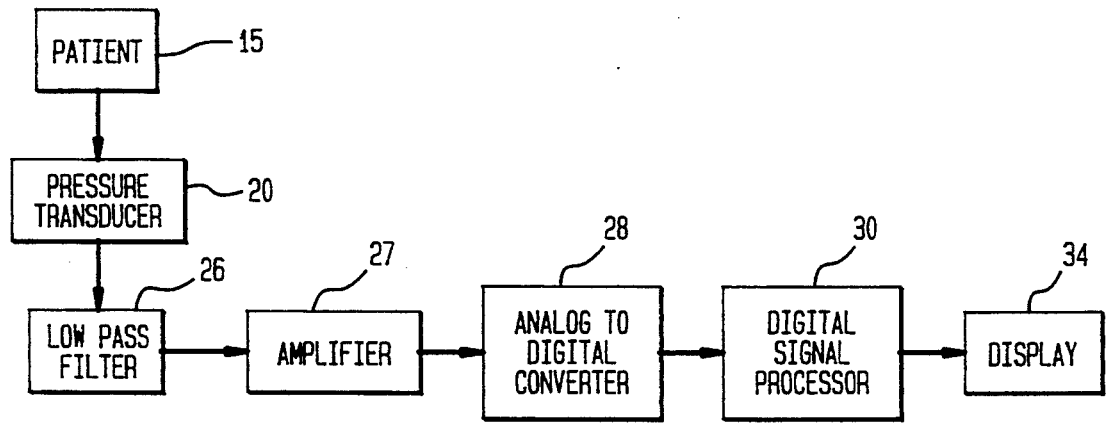
FIG. 4 is a block diagram of parts of the apparatus of the invention.

With reference now to FIG. 4, a block diagram of the apparatus of the invention is shown. Briefly, the arterial blood pressure of a patient is monitored by connecting a catheter that is inserted inside an artery of the patient 15 to a pressure transducer 20; the pressure transducer is connected to a low pass filter 26; the low pass filter is connected to an amplifier 27; the amplifier is connected to an analog to digital converter 28; the analog to digital converter is connected to a digital signal processor 30; the digital signal processor is connected to a display 34.

The low pass filter 26 is set to filter out all signal frequency components that are above a predetermined frequency, and the preferred setting is for the filter to filter out signal frequency components above 50 hz. The amplifier 27 is set to a predetermined fixed gain, and the preferred predetermined fixed gain setting is 311. The analog to digital converter 28 is preferably a 12 bit converter, but a 10 bit converter may be used, albeit with a lower precision. The digital signal processor 30 can be obtained from Analog Devices in Waltham, Mass., and a preferred element is Analog Devices model no. ADSP-2101. The digital signal processor 30 is programmed to carry out the analysis of the arterial pressure waveform as discussed in detail in the next section below.

Figure 5:
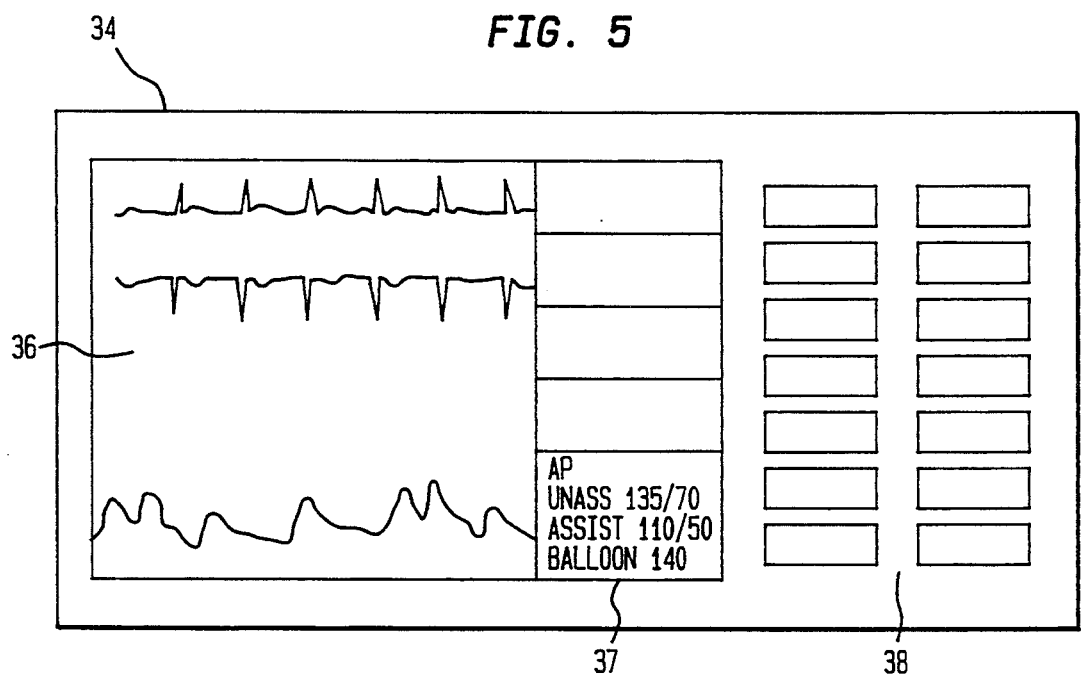
FIG. 5 is a schematic diagram of a display apparatus of the invention.

With reference now to FIG. 5, a display 34 is shown. Display 34 can have a screen portion 36, 37 which displays detected vital signs, including cardiac parameters of a patient as waveforms 36, for example an arterial blood pressure waveform or an ECG waveform, and displays information concerning the detected vital signs of the patient near the displayed waveforms, as can be seen in the boxed regions 37 to the right of the displayed waveforms. The face of the display can also have buttons, shown generally at 38, for the turning on and off of different features of a display, for example, a button could be dedicated to turning on or off the processor to perform the method according to the invention.

Processing of the arterial pressure signal

A pressure value, defined herein as a point, can be determined to be a minimum pressure value if it is the lowest detected point in a set of sampled points and is immediately succeeded by sampled points having increasing values, and this minimum point is validated if the succeeding sampled points increase to a value above a set threshold value. A pressure value (point) can be determined to be a maximum if it is the highest detected point in a set of sampled points and is immediately succeeded by sampled points having decreasing values, and this maximum point is validated if the sampled points decrease below a set threshold value. Once a valid minimum pressure value and a valid maximum pressure value have been identified these pressure values can be used to define a new beat if the minimum point is separated by an interval of time greater than at least 150 msec from the maximum point of the previous valid beat.

The threshold values for minimum and maximum points may be set as follows. The average beat size is determined over time as the difference between the maximum pressure value and minimum pressure value of a beat, and is updated as more data points are collected. The threshold value is set as a fraction of the average beat size, for example, a suitable threshold value is from 0.25 to 0.5 of the average beat size.

The minimum pressure value and maximum pressure value of an arterial blood pressure beat may also be determined in the following manner. The measured arterial blood pressure signal is digitized and the first derivative of the digitized signal determined. A minimum pressure value, defined herein as a point, is then identified as the point at which the first derivative signal crosses zero and the immediately preceding first derivative signal point has a negative value. A maximum pressure value (point) is identified as the point at which the first derivative signal crosses zero and the immediately preceding first derivative signal point has a positive value. The detected minimum pressure value and maximum pressure value are then validated if they are separated by a set threshold value. The threshold value is set as described above.

Using the detected minimum and maximum pressure values, first and second portions of pressure beats in the pressure signal can be determined. Furthermore, in a waveform representation of the beats, areas can be calculated for the first and second portions of the detected beats.

The area of first and second portions of a beat may be determined by any of several methods, two of which are described below. The areas calculated in the first method are shown in FIG. 2A, and the areas calculated in the second method are shown in FIG. 2B.

Figure 2A:
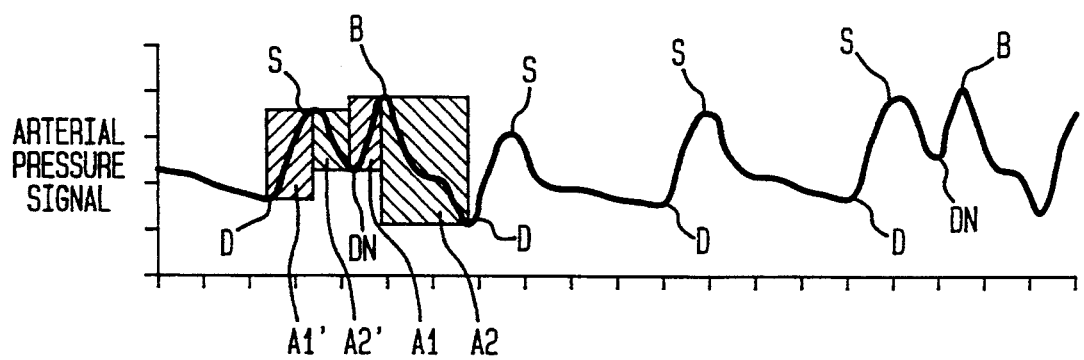
FIG. 2A is a diagram of an arterial blood pressure waveform during intra-aortic balloon assist, with areas associated with first and second portions of a heart beat shaded in order to illustrate one of the two described methods for determining the areas of a beat according to the invention.

Referring to FIG. 2A, the area associated with the first portion of a beat is determined by multiplying the difference in value between the minimum pressure value and maximum pressure value of the first portion of the beat with the time that has elapsed between the occurrence of these pressure values. This first area is shown shaded in FIG. 2A, as A1' for the first beat and A1 for the second beat. The area associated with the second portion of a beat can be determined by multiplying the difference between the maximum pressure value and the next minimum pressure value of the second portion of the beat with the time that has elapsed between the occurrence of these maximum and next minimum pressure values. This second area is shown shaded in FIG. 2A, as A2' for the first beat and A2 for the second beat. This calculation will result in the determination of the area of a rectangle having as two of its diagonal vertices the previously mentioned pressure value, as shown. The symbols D, S, B, and DN in FIG. 2a are the same as described for FIG. 1 above.

Figure 2B:
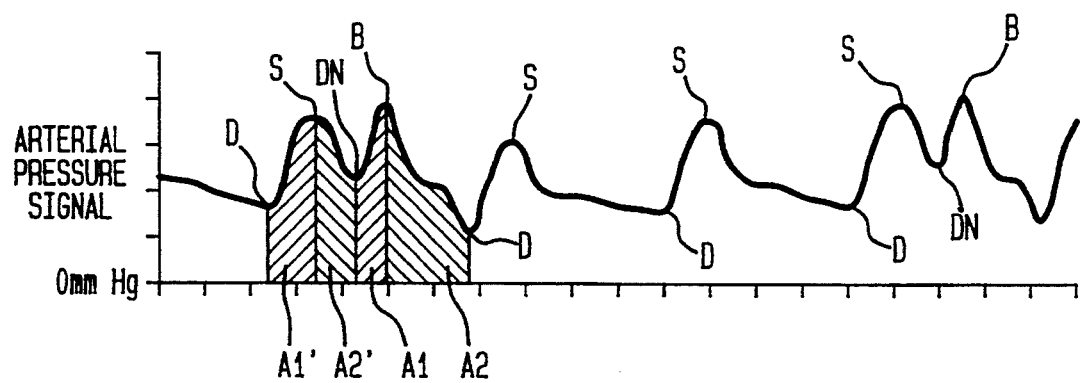
FIG. 2B is a diagram of an arterial blood pressure waveform during intra-aortic balloon assist, with the areas associated with the first and second portions of a heart beat shaded in order to illustrate the other of the two described methods for determining the areas of a beat according to the invention.

Referring now to FIG. 2B, the area associated with the first portion of a beat can also be determined by summing the values of the arterial blood pressure samples from the detected minimum pressure value to the detected maximum pressure value for the first portion of a beat. This first area is shown shaded in FIG. 2B, as A1' for the first beat and A1 for the second beat. The area associated with the second portion of a beat can be determined by summing the values of the arterial blood pressure samples from the maximum pressure value to the next detected minimum pressure value. This second area is shown shaded in FIG. 2B, as A2' for the first beat and A2 for the second beat. This calculation will result in the determination of the area under the waveform, as shown in FIG. 2B. The symbols D, S, B, and DN in FIG. 2B are the same as described for FIG. 1 above.

Figure 6:
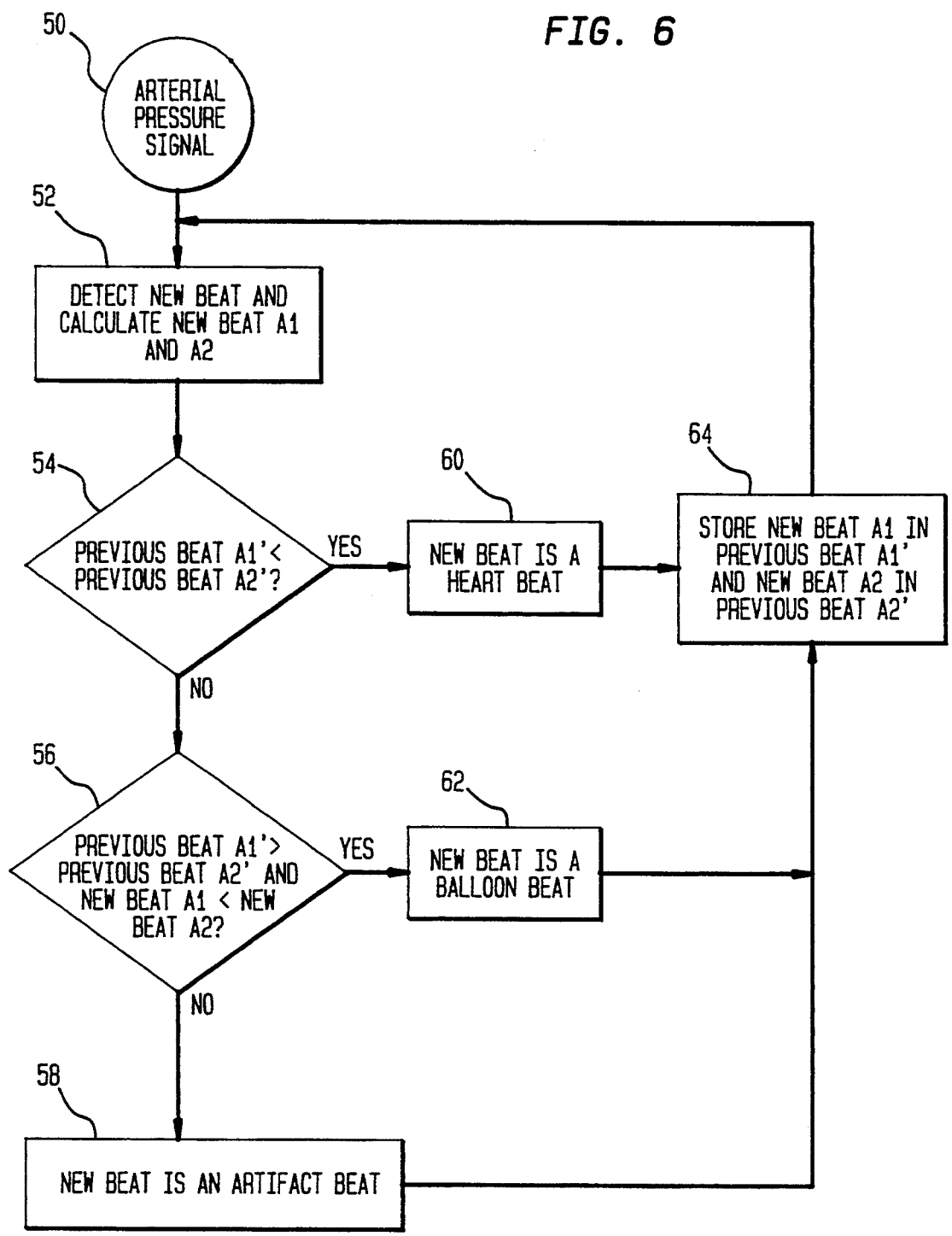
FIG. 6 is a flow chart showing the steps of the identification of a beat as a heart beat or balloon pump beat according to the invention.

The areas associated with the first and second portions of two successive beats are then compared in order to identify a heart beat, a balloon beat and an artifact, as is shown in the flow chart provided in FIG. 6. The arterial pressure signal, here designated as 50, is processed. In this flow chart, the first beat is termed the previous beat, and the second beat is termed the new beat. In step 52 the first area (A1) associated with the first portion of a new beat and the second area (A2) associated with the second portion of the new beat are calculated.

In step 54 the areas associated with the previous beat (A1' and A2') are compared. If previous beat area A1' is less than previous beat area A2' then the new beat is defined as a heart beat in step 60. If previous beat area A1' is greater than previous beat area A2' and new beat area A1 is less than new beat area A2, then the new beat is defined as a balloon beat in step 62. However, if previous beat area A1' is greater than previous beat area A2' and new beat area A1 is greater than new beat area A2, then the new beat is defined as an artifact beat in step 58. This information is stored in step 64, and the comparison of beat portion areas begins again upon the detection of the next new beat.

Upon the determination of a beat as a heart beat, the heart beat can be identified to be either an assisted or an unassisted heart beat as follows. A heart beat is an assisted heart beat if it immediately follows a balloon beat, otherwise a heart beat is an unassisted heart beat.

The average minimum pressure values and maximum pressure values of assisted and unassisted heart beats and the average maximum pressure value of balloon pump beats may be determined once at least eight of a particular type of beat have been identified. Upon determination of at least eight unassisted heart beats, for example, the maximum pressure value, or systolic pressure value, is determined by averaging the maximum unassisted heart beat pressure values after excluding the highest one-quarter of the maximum pressure values and the lowest one-quarter of the maximum pressure values. The minimum pressure value, or diastolic pressure is determined in the same manner.

Determination of heart beat rate

The heart beat rate of a patient who is undergoing an intra-aortic balloon pump assist procedure is determined after identifying beats as intra-aortic balloon pump beats and as heart beats. During the verification of a beat, the time interval between beats must be greater than 150 msec. Thus the interval of time separating two beats is measured, and the interval of time that separates two heart beats, whether assisted or unassisted, is determined. This time interval is measured and recorded as a fraction of a second, the number of heart beats that would be present in one minute is then determined by dividing 60 by the time interval. This resulting value is the heart beat rate or pulse rate of the heart, and the value is displayed for use by the attending health care worker.

Other Embodiments

Other embodiments are within the following claims. For example, a pulse oximetry signal can also be used to find the minimum value and maximum value of heart beats and balloon pump beats, and the described method may be used to identify each beat as an assisted heart beat, an unassisted heart beat, or a balloon pump beat. The pulse oximetry minimum and maximum values may also be used to determine the oxygen saturation of the blood, as is well known in the art. Also, the separation of heart beats from balloon pump beats allows one to determine the correct pulse rate of an individual, as described above.

I claim:

1. Apparatus for identifying heart beats and intra-aortic balloon pump beats during an intra-aortic balloon pump assist procedure, comprising:
    a pressure transducer responsive to arterial blood pressure variations caused by beats during the procedure to generate a corresponding pressure signal;
    circuitry connected to receive the pressure signal from the transducer, the circuitry including:
        processing means responsive to the pressure signal for identifying consecutive beats by determining successive minimum pressure values and maximum pressure values of the pressure signal,
        determining means responsive to the identification of consecutive beats for determining a first and second portion of a beat, wherein the first portion of a beat begins at a minimum pressure value of said pressure signal and ends at an immediately succeeding maximum pressure value of said pressure signal, and wherein the second portion of a beat begins at said maximum pressure value of said pressure signal and ends at an immediately succeeding minimum pressure value of said pressure signal,
        first calculating means responsive to the pressure signal and the determining means for calculating a first value for an attribute of said pressure signal over time during said first portion of a first beat and a second value for said attribute during said second portion of said first beat,
        second calculating means responsive to the pressure signal and the determining means for calculating a first value for an attribute of said pressure signal over time during said first portion of a second beat which consecutively follows said first beat, and a second value for said attribute during said second portion of said second beat,
        first comparing means responsive to said first calculating means for comparing the first value calculated for the first beat with the second value calculated for the first beat,
        second comparing means responsive to said second calculating means for comparing the first value calculated for the second beat with the second value calculated for the second beat,
        identifying means responsive to said first and second comparing means for identifying the second beat as being one of a group consisting of an intra-aortic balloon pump beat, a heart beat and an artifact, means for associating at least one pressure value with said second beat when it is identified as an intra-aortic balloon beat or a heart beat; and display means responsive to said means for associating for displaying said at least one pressure value associated with said second beat.

2. The apparatus of claim 1, wherein:

said identifying means is responsive to said first and second comparing means for identifying the second beat as being an intra-aortic balloon pump beat when the first value calculated for the first beat is greater than the second value calculated for the first beat and the first value calculated for the second beat is less than the second value calculated for the second beat.

3. The apparatus of claim 2, wherein:

said identifying means is responsive to said first and second comparing means for identifying a heart beat as an unassisted heart beat or an assisted heart beat, a heart beat being identified as an assisted heart beat when that beat immediately follows an identified intra-aortic balloon pump beat, and a heart beat being identified as an unassisted heart beat when that beat immediately follows an identified heart beat, said means for associating associates an identified intra-aortic balloon pump beat with a corresponding maximum pressure value, and associates an identified heart beat with both of a corresponding minimum pressure value and a corresponding maximum pressure value, and wherein the display means is responsive to said means for associating for displaying at least one of a minimum pressure value and a maximum pressure value of an unassisted heart beat, a minimum pressure value and a maximum pressure value of an assisted heart beat, and a maximum pressure value of an intra-aortic balloon pump beat.

4. The apparatus of claim 3, including a second determining means responsive to the identifying means and the means for associating for determining an average minimum pressure value and an average maximum pressure value for a plurality of associated identified unassisted heart beats, for determining an average minimum pressure value and an average maximum pressure value for a plurality of associated identified assisted heart beats, and for determining an average maximum pressure value for a plurality of associated identified intra-aortic balloon pump maximum pressure values.

5. The apparatus of claim 4, wherein the second determining means determines an average minimum pressure value of an identified beat by averaging at least eight minimum pressure values of associated identified beats of that beat type after excluding the highest one-quarter and the lowest one-quarter of the minimum pressure values, and determines the average maximum pressure value of an identified beat by averaging at least eight maximum pressure values of associated identified beats of that beat type after excluding the highest one-quarter and the lowest one-quarter of the maximum pressure values.

6. The apparatus of claim 1, including a second determining means responsive to said identifying means for detecting an average heart beat rate based upon a frequency of occurrence of identified heart beats, and wherein said display means is further adapted to display the average heart beat rate.

7. A method for identifying heart beats and intra-aortic balloon pump beats during an intra-aortic balloon pump assist procedure, comprising:

measuring a plurality of arterial pressure values for at least two successive beats during the procedure, determining a first portion and a second portion of each beat, wherein the first portion of a beat begins at a minimum pressure value and ends at an immediately succeeding maximum pressure value, and wherein the second portion of a beat begins at said maximum pressure value and ends at an immediately succeeding minimum pressure value;

processing the measured pressure values to determine respective first and second values calculated from the measured pressure values during the first and second portions of a first of the two successive beats;

processing the pressure values to determine respective first and second values calculated from the measured pressure values during the first and second portions of a second of the two successive beats; and comparing the first value calculated for the first beat with the second value calculated for the first beat, comparing the first value calculated for the second beat with the second value calculated for the second beat, and based upon each of said comparisons, identifying the second beat as being one of an intra-aortic balloon beat, a heart beat or an artifact.

8. The method of claim 7, including the further steps of:

based upon each of the comparisons, identifying the second beat as an intra-aortic balloon pump beat when the first value calculated for the first beat is greater than the second value calculated for the first beat and the first value calculated for the second beat is less than the second value calculated for the second beat, associating an identified intra-aortic balloon pump beat with a corresponding maximum pressure value, associating an identified heart beat with a corresponding minimum pressure value and a corresponding maximum pressure value, and displaying a pressure value associated with an identified beat.

9. The method of claim 8, further comprising:

based upon each of the comparisons, identifying a heart beat as being an assisted heart beat when that beat immediately follows an identified balloon beat, based upon each of the comparisons, identifying a heart beat as being an unassisted heart beat when that beat immediately follows an identified heart beat, associating an identified assisted heart with a corresponding minimum pressure value and a corresponding maximum pressure value, associating an identified unassisted heart beat with a corresponding minimum pressure value and a corresponding maximum pressure value, determining an average minimum pressure value of at least eight sequential unassisted heart beat pressure values after excluding the highest one-quarter of the values and the lowest one-quarter of the minimum pressure values, determining an average maximum pressure value of at least eight sequential unassisted heart beat pressure values after excluding the highest one-quarter of the values and the lowest one-quarter of the values, determining an average minimum pressure value of at least eight sequential assisted heart beat pressure values after excluding the highest one-quarter of the values and the lowest one-quarter of the values, determining an average maximum pressure value of at least eight sequential assisted heart beat pressure values after excluding the highest one-quarter of the values and the lowest one-quarter of the values, and determining an average maximum pressure of at least eight sequential balloon pump beat values after excluding the highest one-quarter of the values and the lowest one-quarter of the values.

10. The method of claim 9, further comprising determining an average heart beat rate based upon a frequency of occurrence for identified heart beats.

11. The method of claim 7, wherein the measuring step comprises invasively measuring said arterial pressure signal.

12. The method of claim 7, wherein the measuring step comprises non-invasively measuring said arterial pressure signal.

13. The method of claim 7, wherein the step of determining first and second portions of each beat comprises determining a first derivative of the plurality of pressure values measured for the at least two successive beats.

14. The method of claim 7, wherein said first value calculated for the first portion of each of the two successive beats is determined by subtracting the minimum value and the immediately succeeding maximum value of the measured arterial pressure occurring during said first portion of a beat for calculating a difference value and multiplying the difference value with a time duration magnitude which exists between the occurrence of said minimum value and said immediately succeeding maximum value.

15. The method of claim 14, wherein said second value calculated for the second portion of each of the two successive beats is determined by subtracting the maximum value and the immediately succeeding minimum value of the measured arterial pressures occurring during said second portion of a beat for calculating a difference value and multiplying the difference value with a time duration magnitude which exists between the occurrence of said maximum value and said immediately succeeding minimum value.

16. The method of claim 7, wherein said first value calculated for the first portion of each of the two successive beats is determined by summing the measured values of the arterial pressure signal, said summing starting at the minimum value and ending at the immediately succeeding maximum value.

17. The method of claim 16, wherein said second value calculated for the second portion of each of the two successive beats is determined by summing the measured values of the arterial pressure signal, said summing starting at said maximum value and ending at the immediately succeeding minimum value.

* * * * *